United States Patent
Farmer et al.

(10) Patent No.: US 11,959,062 B2
(45) Date of Patent: *Apr. 16, 2024

(54) DISTRIBUTED SYSTEMS FOR THE EFFICIENT PRODUCTION AND USE OF MICROBE-BASED COMPOSITIONS

(71) Applicant: LOCUS SOLUTIONS IPCO, LLC, Solon, OH (US)

(72) Inventors: Sean Farmer, Ft. Lauderdale, FL (US); Paul S. Zorner, Encinitas, CA (US); Ken Alibek, Solon, OH (US); Kent Adams, Oro Valley, AZ (US); Tyler Dixon, Madison, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/447,387

(22) Filed: Aug. 10, 2023

(65) Prior Publication Data

US 2023/0383229 A1 Nov. 30, 2023

Related U.S. Application Data

(63) Continuation of application No. 16/331,438, filed as application No. PCT/US2017/050711 on Sep. 8, 2017, now Pat. No. 11,760,969.

(60) Provisional application No. 62/385,057, filed on Sep. 8, 2016.

(51) Int. Cl.
| | |
|---|---|
| C12N 1/14 | (2006.01) |
| C12M 1/00 | (2006.01) |
| C12M 1/34 | (2006.01) |
| C12M 3/00 | (2006.01) |
| C12N 1/16 | (2006.01) |
| C12N 1/20 | (2006.01) |
| C12P 7/64 | (2022.01) |
| C12P 19/44 | (2006.01) |

(52) U.S. Cl.
CPC ............ *C12M 41/26* (2013.01); *C12M 23/44* (2013.01); *C12M 23/52* (2013.01); *C12M 23/58* (2013.01); *C12M 41/12* (2013.01); *C12N 1/14* (2013.01); *C12N 1/16* (2013.01); *C12N 1/20* (2013.01); *C12P 7/64* (2013.01); *C12P 19/44* (2013.01); *Y02A 40/10* (2018.01)

(58) Field of Classification Search
CPC ...... C12M 23/44; C12M 23/52; C12M 23/58; C12M 41/12; C12N 1/14; C12N 1/16; C12N 1/20; C12P 7/64; C12P 19/44; Y02A 40/10

See application file for complete search history.

(56) References Cited

U.S. PATENT DOCUMENTS

| | | | |
|---|---|---|---|
| 4,332,904 A | 6/1982 | Kurane et al. | |
| 4,522,261 A | 6/1985 | McInerney et al. | |
| 6,033,901 A | 3/2000 | Powell, Jr. | |
| 7,556,654 B1 | 7/2009 | Nero | |
| 8,454,983 B2 | 6/2013 | Dechant et al. | |
| 9,441,115 B2 | 9/2016 | Wu et al. | |
| 2008/0107689 A1 | 5/2008 | Seiskari | |
| 2009/0029879 A1 | 1/2009 | Soni et al. | |
| 2009/0186761 A1 | 7/2009 | Arbogast et al. | |
| 2011/0044972 A1 | 2/2011 | Fieldhouse et al. | |
| 2011/0237531 A1 | 9/2011 | Yanagisawa et al. | |
| 2012/0021505 A1 | 1/2012 | Kim et al. | |
| 2012/0058895 A1 | 3/2012 | Awada et al. | |
| 2012/0220464 A1 | 8/2012 | Giessler-Blank et al. | |
| 2013/0062053 A1 | 3/2013 | Kohr et al. | |
| 2013/0324406 A1 | 12/2013 | Chisholm et al. | |
| 2014/0201870 A1 | 7/2014 | Harman | |
| 2014/0273150 A1 | 9/2014 | Angel | |
| 2014/0315765 A1 | 10/2014 | McDaniel | |
| 2014/0323757 A1 | 10/2014 | Kim | |
| 2015/0037302 A1 | 2/2015 | Bralkowski et al. | |
| 2015/0044356 A1 | 2/2015 | Bootsma et al. | |
| 2015/0045290 A1 | 2/2015 | Coutte et al. | |
| 2015/0118203 A1 | 4/2015 | Boyette et al. | |
| 2015/0300139 A1 | 10/2015 | Armstrong et al. | |
| 2015/0305347 A1 | 10/2015 | Wicks et al. | |
| 2016/0040119 A1 | 2/2016 | Hashman | |
| 2016/0083684 A1 | 3/2016 | Li et al. | |
| 2016/0083757 A1 | 3/2016 | Fonseca et al. | |
| 2016/0222280 A1 | 8/2016 | Kohr et al. | |

FOREIGN PATENT DOCUMENTS

| | | |
|---|---|---|
| CN | 101113408 A | 1/2008 |
| CN | 102352227 A | 2/2012 |
| CN | 102613252 A | 8/2012 |
| CN | 102701814 A | 10/2012 |

(Continued)

OTHER PUBLICATIONS

Abdullah, M.T., et al., "Biological control of *Sclerotinia sclerotiorum* (Lib.) de Bary with Trichoderma harzianum and Bacillus amyloliquefaciens." Crop Protection, 2008, 27: 1354-1359.

Adzmi, F., et al. "Preparation, characterisation and viability of encapsulated Trichoderma harzianum UPM40 in alginate-montmorillonite clay." Journal of microencapsulation 29.3 (2012): 205-210.

Alias, N.H., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.

(Continued)

*Primary Examiner* — Kade Ariani

(74) *Attorney, Agent, or Firm* — SALIWANCHIK, LLOYD & EISENSCHENK

(57) ABSTRACT

The invention relates to systems and methods for effective production and use of microorganisms and/or the fermentation broth in which they are produced. Advantageously, the system is cost-effective, scalable, quick, versatile, efficacious, and helpful in reducing resistance to chemical compounds and residue that concerns consumers.

15 Claims, 1 Drawing Sheet

(56) References Cited

FOREIGN PATENT DOCUMENTS

| | | | |
|---|---|---|---|
| CN | 102766579 | A | 11/2012 |
| CN | 102839121 | A | 12/2012 |
| CN | 202849272 | U | 4/2013 |
| CN | 105661630 | A | 6/2016 |
| CN | 105753283 | A | 7/2016 |
| JP | 2014150774 | A | 8/2014 |
| TW | 201237162 | A | 9/2012 |
| WO | 2005059087 | A1 | 6/2005 |
| WO | 2005117929 | A1 | 12/2005 |
| WO | 2009136384 | A2 | 11/2009 |
| WO | 2009136384 | A3 | 11/2009 |
| WO | 2011063129 | A2 | 5/2011 |
| WO | 2011063129 | A3 | 5/2011 |
| WO | 2012010407 | A1 | 1/2012 |
| WO | 2014043058 | A1 | 3/2014 |
| WO | 2014133793 | A1 | 9/2014 |
| WO | 2015089183 | A2 | 6/2015 |
| WO | 2017044953 | A1 | 3/2017 |

OTHER PUBLICATIONS

Amani, H., et al., "Comparative study of biosurfactant producing bacteria in MEOR applications." Journal of Petroleum Science and Engineering. 2010, 75: 209-214.

Cheng, F. Y., et al. "Characterization of a blend-biosurfactant of glycolipid and lipopeptide produced by Bacillus subtilis TU2 isolated from underground oil-extraction wastewater." Journal of microbiology and biotechnology 23.3 (2013): 390-396.

Ciesielska, K., et al., "Exoproteome analysis of Starmerella bombicola results in the discovery of an esterase required for lactonization of sophorolipids." Journal of proteomics, 2014, 98: 159-174.

Coutte, F., et al. "Production of surfactin and fengycin by Bacillus subtilis in a bubbleless membrane bioreactor." Applied Microbiology and Biotechnology 87 (2010): 499-507.

De Almeida, D., et al., "Biosurfactants: Promising Molecules for Petroleum Biotechnology Advances." Frontiers in Microbiology, Oct. 2016, 7(1718): 1-14.

De Boer, Wietse, et al., "Living in a fungal world: impact of fungi on soil bacterial niche development." FEMS Microbiology Reviews, 2005, 29(4): 795-811.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

E Silva, F.C.P.R., et al., "Yeasts and bacterial biosurfactants as demulsifiers for petroleum derivative in seawater emulsions." AMB Expr., 2007, 7(202): 1-13.

Fan, L., et al., "Production and identification of mannosylerythritol lipid-A homologs from the ustilaginomycetous yeast Pseudozyma aphidis ZJUDM34." Carbohydrate Research, 2014, 392: 1-6.

Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.

Gudina, E., et al., "Biosurfactant-producing and oil-degrading Bacillus subtilis strains enhance oil recovery in laboratory sand-pack columns." Journal of Hazardous Materials, 2013, 261: 106-113.

Kulakovskaya, E., et al., "Structure and Occurrence of Yeast Extracellular Glycolipids." Extracellular Glycolipids of Yeasts, eds E. Kulakovskaya and T. Kulakovskaya (Amsterdam: Elsevier), 2014: 1-13.

Kurtzman, C.P., et al., "Production of sophorolipid biosurfactants by multiple species of the Starmerella (Candida) bombicolayeast clade." FEMS Microbiol Lett, 2010, 311: 140-146.

Malusa, E., et al., "Technologies for Beneficial Microorganisms Inocula Used as Biofertilizers." The Scientific World Journal, 2012, vol. 2012, Article ID 491206, pp. 1-12.

Morikawa, M., "Beneficial Biofilm Formation by Industrial Bacteria Bacillus subtilis and Related Species." Journal of Bioscience and Bioengineering, 2006, 101(1): 1-8.

Pacwa-Plociniczak, M. et al., "Review: Environmental Applications of Biosurfactants: Recent Advances." Int. J. Mol. Sci., 2011, 12: 633-654.

Sharma, A. et al., "A study on biosurfactant production in Lactobacillus and *Bacillus* sp." Int. J. Curr. Microbiol. App. Sci., 2014, 3(11): 723-733.

Silva, R., et al., "Applications of Biosurfactants in the Petroleum Industry and the Remediation of Oil Spills." International Journal of Molecular Sciences, 2014, 15: 12523-12542.

Takahashi, M., et al., "Production of Sophorolipid Glycolipid Biosurfactants from Sugarcane Molasses Using Starmerella bombicola NBRC 10243." Journal of Oleo Science, 2011, 60(5): 267-2733.

Definition of facility. According to dictionary.com, retrieved on Jan. 5, 2023.

Definition of modular. According to dictionary.com, retrieved on Jan. 5, 2023.

Definition of module. According to dictionary.com, retrieved on Jan. 5, 2023.

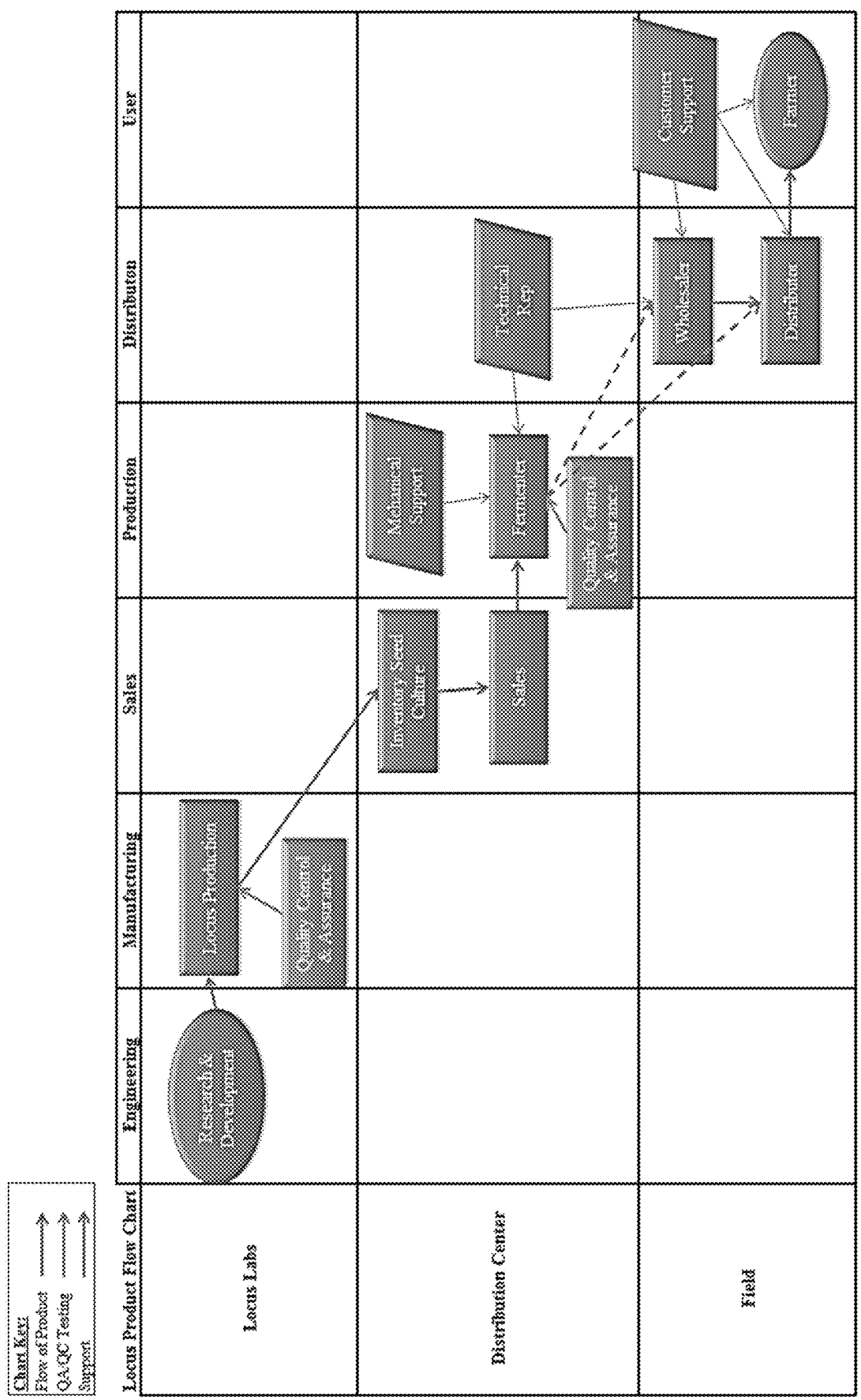

DISTRIBUTED SYSTEMS FOR THE EFFICIENT PRODUCTION AND USE OF MICROBE-BASED COMPOSITIONS

CROSS-REFERENCE TO A RELATED APPLICATION

This application is a continuation application of U.S. patent application Ser. No. 16/331,438, filed Mar. 7, 2019; which is a National Stage Application of International Application No. PCT/US2017/050711, filed Sep. 8, 2017; which claims the benefit of U.S. Provisional Application Ser. No. 62/385,057, filed Sep. 8, 2016, all of which are incorporated herein by reference in their entirety.

BACKGROUND OF INVENTION

Worldwide, farming, forestry, animal husbandry, aquatic farming and other means of producing food, nutritional additives, flavors, fragrances, fiber and natural structural materials is becoming increasingly difficult due to environmental challenges including pest resistance to conventional chemicals, extreme temperatures, droughts, flooding, new plant pathogens and insect pests, the proliferation of transboundary pests, consumer preferences for low chemical residue and non-GMO food and multiple government regulations that limit the broad use of conventional chemical inputs such as herbicides, pesticides and fertilizers in order to limit serious environmental impacts of these same chemical inputs. The seriousness and unpredictability of these factors makes farms, forests, pastures and other production sites very vulnerable and herald the need for greater operational resilience and flexibility. Better management of resources and the ability to increase yields with less input would also put farms, forests and pastures on more resilient footing.

Considering the finite availability of suitable cropland, land suitable for forests, the environmental sensitivity of lands adjacent to these areas, the concerns of communities in which cropland, animal husbandry operations and forest exist, the predominance of rainfed agriculture production, and the additional withdrawals from rivers, lakes, and aquifers to supply future irrigational needs, the increasing scarcity of natural nutrients such as phosphate, minor nutritional elements, etc the spotlight is squarely trained on responsibly increasing crop, forestry and animal yields, productive use of water, as measured by output per unit of land area, and per megaliter of water and per dollar of invested capital all fundamental to achieving food, fiber and structural materials security in the decades to come.

In order to boost yields and protect crops against pathogens, pests, and disease, farmers have relied heavily on the use of synthetic chemicals and chemical fertilizers; however, when overused or improperly applied, these substances can run off into surface water, leach into groundwater, and evaporate into the air. As sources of air and water pollution, these substances are increasingly scrutinized, making their responsible use an ecological and commercial imperative. Even when properly used, the over-dependence and long-term use of certain chemical fertilizers and pesticides deleteriously alters soil ecosystems, reduces stress tolerance, increases pest resistance, and impedes plant and animal growth and vitality.

As synthetic contact nematicide chemistry and soil fumigants face greater scrutiny, and as new nematicide, herbicide, plant growth regulator, insecticide, bactericide, and fungicide and other crop input chemistry pipelines shrink due to increasing regulatory thresholds, sustainable biological pesticides, growth promoting microbes, microbes that increase the nutritional content of soils and help manage water use efficiency are becoming more important alternatives, particularly those that give similar levels of efficacy as the conventional pesticides, fumigants, plant growth regulators, surfactants and fertilizers. Economic and environmental conditions create opportunities for biological treatments of weeds, insects and diseases caused by plant parasitic nematodes, insects, mites, bacteria, and fungi. As a result, there is a significant demand for more environmentally-friendly solutions that makes the investment in research and development of new biologically derived pesticides worthwhile.

$1.5 billion a year is lost to soybean cyst nematode alone. Applying contact nematicides placed in the seed furrow at planting has been the primary application method. Because of toxicity toward animals nearby, such as birds, overhead center pivots with liquid applications of toxic compounds such as Nemacur, Temik, Furadan, Dazinat and Mocap have all fallen out of favor.

Since the 1960's, methyl bromide has been used by growers to effectively sterilize fields before planting to primarily control nematodes, as well as to treat disease and weeds; however, because this toxic compound is used in gas form, more than half the amount injected into soil can eventually end up in the atmosphere. Rising into the atmosphere, it contributes to the thinning of the ozone layer. In 2005, developed countries banned methyl bromide under the Montreal Protocol, which is an international treaty signed in 1987 to protect the stratospheric ozone layer.

Under the ban, the treaty allows limited use of methyl bromide in strawberries, almonds, and other crops that lack alternatives for both effective and affordable control of nematodes, disease, and weeds. The extent of authorized use diminishes every year and will likely end soon. Finding alternatives to methyl bromide is, thus, a priority to the USDA, which provided a $5 million grant that supported research to identify alternatives since 2010. However, no single product provides the wide spectrum of control offered by methyl bromides.

Mounting regulatory mandates governing the availability and use of chemicals and consumer demands for residue free, sustainably-grown food which production has minimal impact on the environment in which that food and fiber is grown are impacting the industry and causing an evolution of thought regarding how to address the myriad of challenges. Clearly, immediately eliminating the use of chemicals is not a viable option. Growers facing the inevitable transition to alternative products are seeking viable alternatives with varying degrees of success. While wholesale elimination of chemicals is not feasible at this time, farmers are increasingly embracing the use of biological measures as viable components of Integrated Nutrient Management and Integrated Pest Management programs.

A plant's nutrition, growth, and proper functioning are dependent on the quantity and distribution of robust populations of natural microflora that in turn, are influenced by soil fertility, tillage, moisture, temperature, aeration, organic matter, and many other factors. Prolonged drought, variable rainfall, and other environmental variations, including the proliferation of nematodes and other pests, and weeds influence those factors and affect soil microflora diversity and plant health.

Also, chemical residues from the foliar or soil application of chemical fertilizers, improperly processed animal wastes used as fertilizers, pesticides, fungicides, herbicides, surfactants and other synthetic products can alter microbial profiles and undermine plant growth and vitality which in turn can impact the animals which consume those plants or products produced from those plants.

The use of biopesticides and other biological agents has been greatly limited by difficulties in production, transportation, administration, pricing and efficacy. For example, many microbes are difficult to grow and subsequently deploy to agricultural and forestry production systems in sufficient quantities to be useful. This problem is exacerbated by loses in viability and/or activity due to processing, formulating, storage, stabilizing prior to distribution, sporulation of vegetative cells as a means of stabilizing, transportation, and application. Furthermore, once applied, biological products may not thrive for any number of reasons including, for example, insufficient initial cell densities, the inability to compete effectively with the existing microflora at a particular location, and being introduced to soil and/or other environmental conditions in which the microbe cannot flourish or even survive—especially if not applied in the environment at concentrations high enough to allow competitive growth with those microbes already present in the environment into which the biological products are released or being fed by nutrients that would be components of innovative biological fertilizers.

"Soft" pesticides, such as those derived from bacteria, yeast or fungi and their metabolites, have been used; however, they are generally weaker and can rapidly leach through the soil, lacking the residual effect to control pests that comes with application of robust, living biological products that continue to produce active metabolites. In point of fact, applying whole broth (the entire fermentation production) can be important to activating and maintaining efficacy of the biological product.

Currently, farming, animal husbandry and forestry operations are limited to sourcing microbial amendments from far-flung producers whose product quality suffers due to upstream processing delays, methods used to stabilize the product for future distribution, supply chain bottlenecks, improper storage, and other factors that inhibit the timely delivery and application of viable, high cell-count microbial products.

Therefore, there is a need for systems and compositions for the efficient production and use of microorganisms and their by-products to empower farmers globally to sustainably grow more food and nutritional supplements, foresters to sustainably produce more fiber and structural materials, better utilize dwindling and scarce natural resources, and bolster operational resiliency and profits.

Microbes and their byproducts are useful in many settings in addition to agriculture, animal husbandry and forestry. These other uses include, but are not limited to, in remediation of soils, water and other natural resources, mining and the oil business, animal feed, waste treatment and disposal, food and beverage preparation and processing, and human health. In each of these settings a readily-available source of microbial cells, spores or mycelia, as well as broth from fermentation of these microbes, can be highly beneficial. There is currently a need for systems that provide such microbe-based products in a way that makes customized products with strong viability readily available to address issues that arise at particular times and at particular locations.

BRIEF SUMMARY

The subject invention provides systems for the efficient production and use of beneficial microbes, as well as for the production and use of substances, such as metabolites, derived from these microbes and the fermentation broth in which they are produced.

The subject invention further provides microbe-based products, as well as uses for these products, that can be used to achieve beneficial results in many settings including, for example, improved bioremediation and mining; waste disposal and treatment; enhancing livestock and other animal health; enhancing oil and gas recovery and cleaning oil and gas processing and transportation equipment; and promoting plant health and productivity by applying one or more of the microbe-based products.

In the context of agriculture, in accordance with the subject invention, it is possible to produce, and efficiently distribute and apply, microbe-based products having advantageous characteristics for a particular crop at a particular time of a growing season and at a particular location.

The systems of the subject invention facilitate obtaining and applying customized microbe-based products that have high concentrations of vegetative cells, reproductive spores, fungal mycelia, and/or other microbial propagules, as well as the broth in which these microbes are grown. The microbial growth by-products in this broth can be highly beneficial in a broad range of agricultural, forestry, pasture and other settings. The microbe-based products can be customized to provide, within days, or less, specific targeted solutions to address particular issues at a specific location.

The microbe-based products of the subject invention can be used in a variety of unique settings because of, for example, the ability to efficiently deliver: 1) fresh fermentation broth with active metabolites; 2) a mixture of cells, spores and/or mycelia and fermentation broth; 3) a composition with vegetative cells, spores and/or mycelia; 4) compositions with a high density of cells, including vegetative cells, spores and/or mycelia; 5) microbe-based products on short-order; and 6) microbe-based products in remote locations.

These microbe-based products can be used in settings including, but not limited to, crops, livestock, forestry, turf management, pastures, aquaculture, mining, waste disposal and treatment, environmental remediation, and human health.

In specific embodiments, the systems of the subject invention provide science-based solutions that improve agricultural productivity by, for example, promoting crop vitality; enhancing crop yields; enhancing insect and disease resistance; controlling insects, nematodes, diseases and weeds; improving plant nutrition; improving the nutritional content of agricultural and forestry and pasture soils; and promoting improved and more efficient water use.

In one embodiment, a system according to the subject invention comprises a first aspect that provides a facility having the capability to produce a plurality of microbe-based compositions; a second aspect for distributing microbe-based products produced at the facility; and, optionally, a third aspect that facilitates field application of the microbe-based products. As used in this context, reference to "field" includes, but is not limited to, agriculture. Thus, the "field" can be any place where the microbe-based products of the subject invention will be used.

Additional aspects of the system can include initial identification and development of microbes, as well as tracking the number and movement of microbes and/or their metabolites post-application.

In one embodiment, the subject invention provides microbial growth facilities having a plurality of microbe growth vessels for cultivation of microorganisms and production of microbial by-products. Preferably, the facility houses at least 2, 25, 50, 75, 110, 250, 500 or more (including every number between 2 and 500 or more) growth vessels, wherein these vessels have independent controls and can be used to cultivate different microorganisms and then transport products of these growth vessels either as single organism products or as mixes of two or more of these products.

The microbe growth facilities of the subject invention produces fresh, microbe-based compositions, comprising the microbes themselves, microbial metabolites, and/or other components of the broth in which the microbes are grown. If desired, the compositions can have a high density of vegetative cells, spores, mycelia, other microbial propagules, or a mixture thereof.

Advantageously, the compositions can be tailored for use at a specified location, with, for example, specified crops, and to address specific issues. In one embodiment, the microbe growth facility is located on, or near, a site where the microbe-based products will be applied to plants, to the environment of plants, or put to other use.

Advantageously, the modular system utilized in the microbe growth facility makes it possible to scale production up or down with low installation or removal expense which could in some embodiments allow movement of the facility from one location to another. The microbe growth facility does not require highly trained personnel for production and a single operator can run many microbe growth systems. Because the products are manufactured in close proximity to the consumer, the time and product damage associated with inventory and distribution are reduced.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown. In the case of agriculture, this capability to dramatically compress the time between manufacture and application empowers farmers to grow more, be more profitable, and to improve the resilience of farm management in the face of mounting climate change impacts, natural resource pressures, changes in regulatory compliance requirements, consumer preferences and other emerging market challenges.

Advantageously, in preferred embodiments, the systems of the subject invention harness the power of naturally-occurring local microorganisms and their metabolic by-products to nourish, invigorate, and protect crop ecosystems and the communities and environments in which these ecosystems exist. Enhancement of local microbial populations can be advantageous in other settings as well, including, but not limited to, environmental remediation (such as in the case of an oil spill), animal husbandry, aquaculture, forestry, pasture management, turf, horticultural ornamental production, waste disposal and treatment, mining, oil recovery, and human health, including in remote locations.

In one embodiment, the system comprises an aspect providing for storage (typically short term storage) and/or distributing the microbe-based products. This aspect of the system can include, for example, a distribution center. In one embodiment, the microbe-based compositions and/or products are stored at the microbe growth facility. In certain embodiments, the distribution center can comprise an inventory center, used for storing the microbe-based products prior to transport to the field of use.

In one embodiment, a distribution center may further comprise a mechanical and/or technical support department that provides mechanical and technical support to customers who, for example, utilize the microbe-based products. The center can provide support for on-site diagnosis, analysis and rectification of issues regarding the microbe-based products and/or their use.

In one embodiment, the system according to the subject invention comprises an additional aspect providing for field application of the microbe-based products. In the case of agriculture, the microbe-based compositions of the subject invention may be applied, for example, through an irrigation system, as a spray, as a seed treatment, to the soil surface, to plant surfaces, and/or to pest surfaces. Mechanical application through conventional implements or robotic application through aerial or ground based "drones" is also facilitated.

Advantageously, the systems of the current invention provide consumers, through novel technologies involving cost-effective approaches, fresh, potent, high cell-count microbe-based compositions, which can include metabolites and/or other by-products produced during the cultivation process. Furthermore, these microbe-based products can be specifically tailored and produced with a short lead time, to meet the immediate needs of a specific farm or other consumer.

Thus, the distributed systems of the subject invention facilitate the custom production of microbes, mixtures of microbes, fermentation broths, and mixtures thereof, to meet the needs of consumers in a particular geographic location with specific needs for enhancing yields, efficiency or other goals.

BRIEF DESCRIPTION OF DRAWINGS

FIG. 1. Flow chart of a system for effective production and use of microorganisms and the by-products of microbial growth.

DETAILED DISCLOSURE

The subject invention provides systems for the efficient production and use of beneficial microbes, as well as for the production and use of substances, such as metabolites, produced by these microbes.

In a preferred embodiment, the subject invention provides microbe-based compositions, as well as methods of using the compositions for promoting plant health, soil microbial diversity, plant nutrition, soil nutritive capacity, optimizing soil moisture status, soil aeration, soil water holding capacity and reducing the susceptibility of plants, to pests, diseases and weeds. This is achieved by improving a plant's natural defenses, the nutritive content, the microbial health of soils as well as by directly impacting plant pests, diseases or weeds. This plant-promotion effect occurs as a result of applying one or more of the microbe-based products of the subject invention to the plant and/or its environment.

Thus, in certain embodiments, the subject invention provides compositions and methods for improving a plant's defense against exogenous attacks by employing one or more microbes and/or microbe-based compositions. The exogenous attacks can be biotic or abiotic in nature. Non-limiting examples of biotic attacks include plant parasites, herbivores, insects, insects which serve as vectors of plant disease, bacteria, fungi, virus and invasive plants such as weeds. Abiotic attacks can be caused by, for example, changes in a plant's environment. In some embodiments, the exogenous attacks are abiotic, originating from extreme physical conditions that include, but are not limited to, changes in temperature, light exposure, salinity, nutrition, water quality, water availability, aeration, soil quality, and other factors affecting the target plant's growth.

In one embodiment, the system according to the subject invention comprises an efficient chain of producing, distributing, and using microbe-based products. The products can comprise the microorganisms themselves, as well as the by-products of their growth. In preferred embodiments, the system comprises facilities and equipment that promote the production, distribution and utilization of the microbe-based products. These facilities can include, but are not limited to production, storage and distribution facilities.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with broth in which they were grown, in the microbe-based composition. The cells may be present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more propagules per milliliter of the composition. As used herein, a propagule is any portion of a microorganism from which a new and/or mature organism can develop, including but not limited to, cells, spores, mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

In accordance with the subject invention, it is possible to produce, and efficiently distribute and apply, microbe-based products having advantageous characteristics for, for example, a particular crop at a particular time of a growing season and at a particular location. Thus, in one embodiment, the systems of the subject invention provide science-based solutions that improve agricultural productivity by, for example, promoting crop vitality, enhancing insect and disease resistance, and promoting improved responses to water stress, salt stress, aeration stress or nutritional deficiency.

Distributed Systems for Production and Use of Microbe-Based Products

The subject invention provides a system for providing microbes and/or microbe-based products for application in a specific setting and/or environment, wherein the system comprises:
(i) a microbe growth facility comprising a plurality of modular growth vessels in which the same, or different, microbes can be grown, under the same, or different, growth conditions to produce a microbe-based composition from each growth vessel, wherein the growth medium, oxygenation, pH, agitation, and/or temperature can be independently and/or jointly controlled for each of said growth vessels; and wherein the microbe-based composition is harvested thereby creating a microbe-based product that can, optionally, have additional components added to produce a microbe-based product that can then be provided to the consumer; and
(ii) a transportation component for transporting said microbe-based product(s) produced in the microbe growth facility, wherein said transportation component comprises containers and/or conduits to transport the microbe-based product(s) from the microbe growth facility to a distribution center or to a location where the microbe-based product will be used.

As used herein, "harvested" refers to removing some or all of the microbe-based composition from the growth vessel. FIG. 1 is a flowchart showing the components of one embodiment of the present invention. Although the components are shown in serial fashion for ease of explanation, there is no sequential limitation implied other than indicated in the appended claims. In addition, some components may be optional.

In one embodiment, the subject invention provides systems for identifying and developing agriculturally-useful strains of microorganisms; growing such microorganisms to produce, locally and at a desired scale, microbe-based compositions having desired characteristics when applied to plants or their environment; making microbe-based products readily and efficiently available to consumers; and using such products to promote plant health, yield, vitality and market appeal.

In one embodiment, the system for the efficient production and use of microorganisms comprises: 1) identifying and/or developing a microorganisms of interest; 2) generating a fermentable and genetically stable strain of the microorganism; 3) growing a specific strain of the microorganism in either pure form or with other microorganisms; 4) distributing the microorganisms and/or its growth by-product to a customer; 5) applying the microorganism in its field of use.

The system according to the subject invention can comprise an aspect responsible for product development including, for example, development, identification and/or characterization of microorganisms and/or microbial metabolites. The product development may be an in-house research lab or a collaboration with another research facility. Microorganisms may be identified, developed, optionally modified, and tested with respect to their various properties (e.g., pest control properties, the ability to produce a metabolite of interest, ability to grow in a particular environment, nutrient requirements, etc.). The system of the subject invention may also comprise an innovation center equipped and staffed to meet the distinct and variable needs of consumers in a particular area.

The consumers may be, for example, farmers, foresters, grasslands, ornamental producers, turf grass managers, mining and/or drilling operations, environmental site managers, park and other managers of natural sites, waste treatment operators, feedlots and other animal husbandry or aquaculture operations, and bioremediation sites.

Microbe Growth Facilities

In preferred embodiments of the subject invention, a microbe growth facility produces fresh, high-density microorganisms and/or microbial growth by-products of interest on a desired scale. The microbe growth facility 6 may be located at or near the site of application. The facility produces high-density microbe-based compositions in batch, quasi-continuous, or continuous cultivation.

The distributed microbe growth facilities of the subject invention can be located at the location where the microbe-based product will be used (e.g., farm, forest, pasture, feedlot, mining, waste treatment, park, remediation, or aquaculture facility) or near the location of use. For example, the microbe growth facility may be less than 300, 250, 200, 150, 100, 75, 50, 25, 15, 10, 5, 3, or 1 mile from the location of use.

Because the microbe-based product is generated locally, without resort to the microorganism stabilization, preservation, storage and transportation processes of conventional microbial production, a much higher density of live microbes in a vegetative, spore and/or mycelial state can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients, pH control agents, and defoaming agents) that makes the system efficient. Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization, have been sporulated or sat in the supply chain for some time. The microbe-based products of the subject invention are particularly advantageous compared to traditional products wherein cells, spores or mycelia have been separated from metabolites and nutrients present in the fermentation growth media. Reduced transportation times allow for the production and delivery of fresh batches of microbes and/or their metabolites at the time and volume as required by local demand.

In preferred embodiments, the facility 6 houses production systems that are modular in design and cost-effectively allow for rapid and unlimited scaling. Moreover, the microbe growth facilities support the production of multiple strains of microbes in order to meet the diverse and changing needs of the customers geographically close to the production facility.

In a single microbe growth facility (e.g., a building) there may be, for example, 2, 5, 10, 20, 50, 75, or 100 or more microbial growth vessels. The vessels may be of different volumes and utilize different growth media and growing conditions and principles. The growth vessels can be added or removed as needed. They can be moved to a new location. Preferably, each growth vessel has its own controls and measuring systems for at least temperature and pH. In addition to monitoring and controlling temperature and pH, each vessel may optionally also have the capability for monitoring and controlling, for example, dissolved oxygen, agitation, foaming, purity of microbial cultures, production of desired metabolites and the like.

In one embodiment, a single type of microbe is grown in a vessel. In alternative embodiments, multiple microbes, which can be grown together without deleterious effects on growth or the resulting product, can be grown in a single vessel. There may be, for example, 2 to 3 or more different microbes grown in a single vessel at the same time.

The growth vessel may be, for example, from 5 liters to 2,000 liters or more. Typically, the vessels will be from 10 to 1,500 liters, and preferably are from 100 to 1,000 liters, and more preferably from 250 to 750 liters, or from 400 to 600 liters. A variety of growth systems can be utilized within these growth vessels.

These vessels may be, for example, made of glass, polymers, metals, metal alloys, and combinations thereof. Prior to microbe growth, the vessel may be disinfected or sterilized.

Advantageously, the use of multiple independent growth vessels has the advantage of limited damage and economic loss if one of the growth vessels has a mechanical problem and/or one of the batches goes bad.

The cultivation time for the individual vessels may be, for example, from 1 to 7 days or longer. The cultivation product can be harvested in any of a number of different ways.

Because the microbe-based product is generated on-site or near the site of application, without the requirement of stabilization, preservation, prolonged storage and extensive transportation processes of conventional production, a much higher density of live microorganisms can be generated, thereby requiring a much smaller volume of the microbe-based product for use in an on-site application. This allows for a scaled-down bioreactor (e.g., smaller fermentation tank, smaller supplies of starter material, nutrients, pH control agents, and de-foaming agent, etc.), no reason to stabilize the cells or separate them from their culture broth and facilitates the portability of the product.

The microbe growth facilities provide manufacturing versatility by the ability to tailor the microbe-based products to improve synergies with destination geographies, regardless of topography, crop or animal type, soil profile, climate, pests, etc. For example, fermentation times typically range from one to six days facilitating a rapid response to "in season" issues that threaten crops.

Production of multiple strains of microbes at the microbial growth facilities of the subject invention facilitates providing a broad portfolio of products to the consumers. The system is able to provide customized microbes for the needs and current conditions of that location and job.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver innovations capable of bolstering yields and improving microbe performance. In the case of agriculture, this can lead to improving the quality of, for example, high value crops, managed turf, and ornamentals.

Methods for the Production of Microorganisms

The subject invention provides methods for cultivation of microorganisms and production of microbial metabolites and/or other by-products of microbial growth. The subject invention further provides cultivation processes that are suitable for cultivation of microorganisms and production of microbial metabolites on a desired scale. These cultivation processes include, but are not limited to, submerged cultivation/fermentation, surface cultivation, solid state fermentation (SSF), and/or combinations thereof, and can be carried out as aerobic or anaerobic processes.

In one embodiment, the subject invention provides materials and methods for the production of biomass (e.g., viable cellular material), extracellular metabolites (e.g., small molecules and excreted proteins), residual nutrients and/or intracellular components (e.g., enzymes and other proteins).

The microbial cultivation systems would typically use submerged culture fermentation; however, surface culture and hybrid systems can also be used. As used herein "fermentation" refers to growth of cells under controlled conditions. The growth could be aerobic or anaerobic.

The microbe growth vessel used according to the subject invention can be any fermenter or cultivation reactor for industrial use. The cultivation process is carried out in a vessel that may be, for example, conical or tubular. In one embodiment, the vessel may optionally have functional controls/sensors or may optionally be connected to functional controls/sensors to measure important factors in the cultivation process, such as pH, oxygen, pressure, temperature, agitator shaft power, humidity, viscosity and/or microbial density and/or metabolite concentration. In some embodiments, cultivation can proceed without stabilization or monitoring of fermentation conditions.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before, and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention further provides a method for producing microbial metabolites such as proteins, peptides, metabolic intermediates, polyunsaturated fatty acid, and lipids. The metabolite content produced by the method can be, for example, at least 20%, 30%, 40%, 50%, 60%, 70%, 80%, or 90%.

The biomass content of the fermentation broth may be, for example from 5 g/l to 180 g/l or more. In one embodiment, the solids content of the broth is from 10 g/l to 150 g/l.

In one embodiment, the method for producing a microbial metabolite according to the subject invention comprises the steps of: 1) mixing hydrophobic and hydrophilic particles to form a matrix-forming solid substance; 2) contacting said matrix-forming solid substance with a medium inoculated with a microorganism of interest, thereby creating a matrix of micro-reactors; 3) growing said microorganism within said micro-reactors; and 4) harvesting said metabolite produced by said microorganism.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification. If desired, extraction and purification can be easily achieved using standard extraction methods or techniques described in the literature.

The microorganisms in the microbe-based product may be in an active or inactive form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, nutrients for plant growth, tracking agents, pesticides, herbicides, animal feed, food products and other ingredients specific for an intended use.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

The microbe-based products of the subject invention may be, for example, microbial inoculants, biopesticides, nutrient sources, remediation agents, health products, and/or biosurfactants.

Distribution of Microbe-Based Products

The system optionally comprises an aspect for distributing the microbe-based product. In one embodiment, this aspect includes a distribution center 3 that can optionally comprise an inventory center 4. The inventory center 4 can be responsible for storing and further distributing the microbe-based products. The inventory center can provide customer support including, for example, consulting with customers regarding delivered and available microorganism inoculums.

In one embodiment, the distribution center 3 may provide services relating to the sale, storage, and transportation of the microbe-based products. The distribution center 3 may also provide mechanical and technical support.

Application of Microbe-Based Products

In yet another aspect, the methods and systems of the subject invention can include methods, systems, and devices for applying the microbe-based products.

In the case of agriculture, the compositions may be, for example, introduced into an irrigation system, sprayed from a backpack or similar devices, applied by a land based or airborne robotic device such as a drone, and/or applied with a seed. Seed application may be by, for example, a seed coating or by applying the composition to the soil contemporaneously with the planting of seeds. This may be automated by, for example, providing a device or an irrigation system that applies the microbe-based composition along with, and/or adjacent to, seeds at, or near, the time of planting the seeds. Thus, the microbe-based composition can be applied within, for example, 5, 4, 3, 2, or 1 day before or after the time of plantings or simultaneously with planting of the seeds.

In some agricultural embodiments, the compositions provided herein, either in a dry or in liquid formulation, are applied as a seed treatment or to the soil surface, to the surface of a plant and/or to the surface of a pest or weed.

In certain embodiments, the compositions provided herein are applied to the soil surface without mechanical incorporation. The beneficial effect of the soil application can be activated by rainfall, sprinkler, flood, or drip irrigation, and subsequently delivered to, for example, targeted pests in order to drive their population levels down to acceptable thresholds or to the roots of plants to influence the root microbiome or facilitate uptake of the microbial product into the vascular system of the crop or plant to which the microbial product is applied. In an exemplary embodiment, the compositions provided herein can be efficiently applied via a center pivot irrigation system or with a spray over the seed furrow.

Reference herein to administration of the composition "on or near" a pest or a plant, or to the "environment" of a pest or plant, means that the administration is such that the composition is sufficiently in contact with the pest or plant such that the desired result (e.g., killing the pest, increasing yield, preventing damage to the plant, regulating genes and/or hormones, etc.) is achieved. This may typically be within, for example, 10, 5, 3, 2, or 1 feet or less, of the pest, plant, weed, or other desired target.

The microbe-based product may also be applied so as to promote colonization of the roots and/or rhizosphere as well as the vascular system of the plant in order to promote plant health and vitality. Thus, nutrient-fixing microbes such as rhizohium and/or mycorrhzae can be promoted as well as other endogenous (already present in the soil), as well as exogenous, microbes, or their by-products, that combat pests, weeds, or disease, or otherwise promote crop growth, health and/or yield. The microbe-based product can also support a plant's vascular system by, for example, entering and colonizing said vascular system and contributing metabolites, and nutrients important to plant health and productivity or metabolites with pest controlling properties.

Advantageously, the method does not require complicated equipment or high energy consumption. The microorganisms of interest can be cultivated at small or large scale on site and utilized, even being still mixed with their media. Similarly, the microbial metabolites can also be produced at large quantities at the site of need.

Advantageously, the microbe-based products can be produced in remote locations. In one embodiment, the microbe-based products can be used for human nutrition and/or disease prevention and/or treatment. The microbe growth facilities may operate off the grid by utilizing, for example, solar, wind and/or hydroelectric power.

The microbe-based products may be applied directly to animal waste, and/or used in a waste treatment plant. The microbe-based products can also be applied directly to environment contamination such as an oil spill or hazardous waste site. The microbe-based products can also be applied to ores in order to recover metals, minerals, or other substances of interest. The microbe-based products can also be injected into oil wells and/or the piping, tanks and other equipment associated with oil wells and/or oil processing. Thus, the field of use includes oil rigs, oil storage facilities, transmission pipelines, tankers and refineries.

Microbial Inoculants

In one embodiment, the microbe-based product is a microbial inoculant. When applied to, for example, seed, plant, or soil of row crops, forestry operations, managed pastures, horticulture crops, managed turf, animal waste and/or animal feeds the inoculant becomes an integral part of the property of the host soil or host medium and promotes the healthy growth of indigenous, beneficial microorganisms that benefit that soil or medium or plants and animals that are grown, fed or otherwise exposed to these soils and media. Once applied to the soil, microbial inoculants of the subject invention improve the mineralization of organic matter, increase nitrogen fixation needed for photosynthesis, increase phosphorous availability to crops while limiting its environmental leaching, produce beneficial plant signaling metabolites, stimulate root mass facilitating uptake of water and key nutrients, improve soil fertility, and/or boost biomass.

In one embodiment, the inoculants can be customized by crop or geography to facilitate the robust colonization of beneficial microorganisms, which makes this technology ideal for proactively managing specific crops grown in vastly different soil ecosystems. The ability to customize microbials to suit the needs of different soil ecosystems becomes even more important as a better understanding is developed of how complex microbial communities react to extreme temperatures, prolonged drought, variable rainfall, and other impacts stemming from climate change and intensive farming.

Because of the high density of vegetative cells, spores, mycelia and/or other microbial propagules, in certain embodiments of the subject invention, the microbe-based products of the subject invention are uniquely advantageous in their ability to colonize an environment, such as soil, and to interact in a favorable fashion with the existing microflora. Due to the exceptional high cell, spore, and/or mycelia counts, the microbe-based products of the subject invention make it possible for extended survival of the microbes in the soil (or other relevant environment). This survival can be further enhanced and extended by, for example, providing the microbes with nutrients.

In one embodiment of the subject invention, the survival and retention of the microbes is monitored by tracking and/or quantifying the microbes and/or their movement in the soil or other environment.

Biocontrol Agents

In another embodiment, the microbe-based product is a biocontrol agent. Compared to conventional synthetic chemical pesticides that can pollute the environment and adversely affect non-target plants and animals, biopesticides are non-toxic, safe to use, and can have high specificity. Best used as a preventative rather than curative tool to manage weeds, diseases, nematodes and insects and other pests, biopesticides allow farmers to reduce their traditionally heavy reliance on chemical-based pesticides and herbicides without affecting crop yields. Biopesticides help create an environmental where pests are unable to gain a foothold and thrive, which is a critical benefit given the proliferation of agricultural pests linked to extreme weather. Use of biopesticides also enables farmers to reduce soil contamination for rotational crops, toxicity to non-target plants and animals, crop toxicity, development of pesticide resistance and runoff and leaching to environmentally sensitive areas, water supplies, etc. and other consequences of using chemical pesticides.

Resistance to chemically-based pesticides is of major concern as resistant pests and insects threaten agricultural productivity and are costly to combat once resistance develops.

Soil Amendments

In one embodiment, the microbe-based product is a soil amendment for use in enhancing the health, growth and yields of plants and/or crops in, for example, agriculture, horticulture, greenhouses, landscaping, and the like. The present invention can also be used for improving one or more qualities of soil, thereby enhancing the performance of the soils for agricultural, home and gardening purposes.

As used herein, "enhancing" means improving or increasing. For example, enhanced plant health means improving the plant's ability grow and thrive, including the plant's ability to ward off pests and/or diseases, and the plant's ability to survive droughts and/or overwatering. Enhanced plant growth means increasing the size and/or mass of a plant, or improving the ability of the plant to reach a desired size and/or mass. Enhanced yields mean improving the end products produced by the plants in a crop, for example, by increasing the number of fruits per plant, increasing the size of the fruits, and/or improving the quality of the fruits (e.g., taste, texture).

As used herein, a "soil amendment" or a "soil conditioner" is any compound, material, or combination of compounds or materials that are added into soil to enhance the physical properties of the soil. Soil amendments can include organic and inorganic matter, and can further include, for example, fertilizers, pesticides and/or herbicides. Nutrient-rich, well-draining soil is essential for the growth and health of plants, and thus, soil amendments can be used for enhancing the growth and health of plants by altering the nutrient and moisture content of soil. Soil amendments can also be used for improving many different qualities of soil, including but not limited to, soil structure (e.g., preventing compaction); improving the nutrient concentration and storage capabilities; improving water retention in dry soils; and improving drainage in waterlogged soils.

In preferred embodiments, the subject methods comprise applying a microbe-based product, i.e., a microbe-based soil amendment, to soil in which a plant or crop grows or will be planted. The microbe-based product can comprise a microorganism and/or a growth by-product of the microorganism. In preferred embodiments, the growth by-product is a sophorolipid biosurfactant.

In some agricultural embodiments, the compositions provided herein, either in a dry or in liquid formulation, are applied as a seed treatment or to the soil surface, or to the surface of a plant (e.g., to the surface of the plant root).

In certain embodiments, the compositions provided herein are applied to the soil surface without mechanical incorporation. The beneficial effect of the soil application can be activated by rainfall, sprinkler, flood, or drip irrigation, and subsequently delivered to, for example, the roots of plants to influence the root microbiome or facilitate uptake of the microbial product into the vascular system of the crop or plant to which the microbial product is applied. In an exemplary embodiment, the compositions provided herein can be efficiently applied via a center pivot irrigation system or with a spray over the seed furrow.

The microbe-based product may also be applied so as to promote colonization of the roots and/or rhizosphere as well as the vascular system of the plant in order to promote plant health and vitality. Thus, nutrient-fixing microbes such as rhizohium and/or mycorrhzae can be promoted as well as other endogenous (already present in the soil), as well as exogenous, microbes, or their by-products that promote crop growth, health and/or yield. The microbe-based product can also support a plant's vascular system by, for example, entering and colonizing said vascular system and contributing metabolites, and nutrients important to plant health and productivity.

Soils can be treated at any point during the process of cultivating the plant. For example, the microbe-based product can be applied to the soil prior to when seeds are planted therein, or at any point thereafter during the development and growth of the plant or plants.

In some embodiments, the method comprises contacting the soil with the microorganism in combination with the biosurfactants it produces. The microbes can be either live (or viable) or inactive at the time of application. The methods can further comprise adding materials to enhance microbe growth during application (e.g., adding nutrients to promote microbial growth). In one embodiment, the nutrient sources can include, for example, nitrogen, nitrate, phosphorus, magnesium and/or carbon.

In other embodiments, the method comprises simply applying biosurfactants to the soil without the microbes.

In one embodiment, the method comprises applying a microbe-based product comprising *Starmerella bombicola* yeast and/or its growth by-products to soil, wherein the composition allows for enhanced absorption of water and/or nutrients from the soil. In one embodiment, the microorganism of the microbe-based product is *Wickerhamomyces anomalus*. In yet another embodiment, the microbe-based product comprises SLP without the microorganism. Advantageously, the methods improve plant health, growth and/or yields without use of harsh chemicals.

The subject invention can be used to improve any number of qualities in any type of soil, for example, clay, sandy, silty, peaty, chalky, loam soil, and/or combinations thereof. Furthermore, the methods and compositions can be used for improving the quality of dry, waterlogged, porous, depleted, compacted soils and/or combinations thereof.

In one embodiment, the method can be used for improving the drainage and/or dispersal of water in waterlogged soils. In one embodiment, the method can be used for improving water retention in dry soil.

In one embodiment, the method can be used for improving nutrient retention in porous and/or depleted soils.

The microbe-based products can be used either alone or in combination with other compounds for efficient enhancement of plant health, growth and/or yields. For example, commercial and/or natural fertilizers, pesticides, herbicides and/or other soil amendments can be applied alongside the microbe-based product. In certain embodiments, the microbe-based products can be used to enhance the effectiveness of the other compounds, for example, by promoting the retention of the compound in soil, or allowing for more uniform dispersal of the compound throughout the soil.

In other applications, desired soil attributes may be obtained by mixing a variety of materials into the soil including, for example, bone meal, alfalfa, corn gluten, potash, and/or manure from a variety of animals including horses, cows, pigs, chickens, bats, sheep. Other additional elements that can be added include, but are not limited to, mineral nutrients such as magnesium, phosphate, nitrogen, potassium, selenium, calcium, sulfur, iron, copper, and zinc. The exact materials and the quantities thereof can be determined by a soil scientist.

Biosurfactants

In one embodiment, the microbe-based product comprises a biosurfactant. Microbial biosurfactants are compounds produced by a variety of microorganisms such as bacteria, fungi, and yeasts. Biosurfactants form an important class of secondary metabolites that occur in many microorganisms such as *Starmerella* species, *Pichia* species, *Pseudomonas* species (*P. aeruginosa, P. putida, P. florescens, P. fragi, P. syringae*); *Flavobacterium* spp.; *Bacillus* spp. (*B. subtilis, B. pumillus, B. cereus, B. licheniformis*); *Candida* species (*C. albicans, C. rugosa, C. tropicalis, C. lipolytica, C. torulopsis*); *Rhodococcus* sp.; *Arthrobacter* spp.; *campylobacter* spp.; *Cornybacterium* spp. and so on. Safe, effective microbial bio-surfactants reduce the surface and interfacial tensions between the molecules of liquids, solids, and gases. This dynamic can be used to facilitate plant health, increase yields, manage soil aeration, and responsibly utilize available irrigation water resources.

Thus, in one embodiment, the microbe-based product improves the health and productivity of plants undergoing water stress.

Biosurfactants are unique in that they are produced via microbial fermentation but have those properties possessed by chemical surfactants in addition to other attributes not possessed by their synthetic analogs. Biosurfactants decrease the tendency of water to 'pool', they improve the 'adherence' or 'wettability' of surfaces, which results in more thorough hydration of the full rhizosphere, and they reduce the volume of water that might otherwise 'escape' below the root zone via micro-channels formed by drip and micro-irrigation systems. This 'wettability' also promotes better root system health as there are fewer zones of desiccation (or extreme dryness) inhibiting proper root growth and better availability of applied nutrients as chemical and micro-nutrients are more thoroughly made available and distributed.

The more uniform distribution of water in the crop rhizosphere made possible by enhanced 'wettability' also prevents water from accumulating or getting 'trapped' above optimal penetration levels thereby mitigating anaerobic conditions that inhibit the free exchange of oxygen and carbon. Once an efficacious biosurfactant is applied a more porous or 'breathable' crop rhizosphere is established and roots will have greater resistance to soil borne disease. The combination of a properly hydrated and aerated rhizosphere also increases the susceptibility of soil pests and pathogens (such as nematodes and soil borne fungi and their spores) to chemical pesticides and biopesticides. Biosurfactants can be used for a wide range of useful applications include disease and pest control Biosurfactants produced according to the subject invention can be used for other, non-agriculture purposes including, for example, cleaning pipes, reactors, and other machinery or surfaces.

Biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes.

Biosurfactants are biodegradable and can be easily and cheaply produced using selected organisms on renewable substrates. Most biosurfactant-producing organisms produce biosurfactants in response to the presence of hydrocarbon source (e.g., oils, sugar, glycerol, etc) in the growing media. Other media components such as concentration of iron can also affect biosurfactant production significantly.

In one embodiment, the microbial biosurfactant is a glycolipid such as a rhamnolipid, sophorolipids (SLP), trehalose lipid or mannosylerythrithol lipid (MEL).

Microbial Factories

The microbes and their growth products produced according to the subject invention can be used to produce a vast array of useful products, including, for example, biopesticides, biosurfactants, ethanol, nutritional compounds, therapeutic proteins such as insulin, compounds useful as vaccines, and other biopolymers. The microbes used as these microbial factories may be natural, mutated or recombinant.

Microorganisms Grown in Accordance with the Subject Invention

The microorganisms grown according to the systems and methods of the subject invention can be, for example, bacteria, yeast, and/or fungi. These microorganisms may be natural, or genetically modified microorganisms. For example, the microorganisms may be transformed with specific genes to exhibit specific characteristics.

In specific embodiments, the microorganisms are bacteria, including gram-positive and gram-negative bacteria. The bacteria may be, for example *Bacillus firmus, Bacillus laterosporus, Bacillus megaterium, Bacillus amyloliquifaciens, Azobacter vinelandii, Pseudomonas chlororaphis* subsp. *aureofaciens (Kluyver), Agrobacterium radiobacter, Azospirillum brasiliensis, Azobacter chroococcum, Rhizobium, Sphingomonas paucimobilis, Ralsonia eulropha, Clostridium (C. butyricum, C. tyrobutyricum, C. acetobutyricum, Clostridium* NIPER 7, and *C. beijerinckii*) and/or *Rhodospirillum rubrum*.

In another embodiment, the microorganism is a yeast or fungus. Yeast and fungus species suitable for use according to the current invention, include *Candida, Saccharomyces cerevisiae, Saccharomyces boulardii sequela* and *Saccharomyces torula, Issalchenkia, Kluyveromyces, Pichia, Wickerhamomyces, Starmerella, Mycorrhiza, Mortierella, Phycomyces, Blakeslea, Thraustochytrium, Phythium, Entomophthora, Aureobasidium pullulans, Fusarium venenalum, Aspergillus, Trichoderma reesei*, and/or *Rhizopus* spp.

In one embodiment, the yeast is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Examples of killer yeasts according to the present invention are those that can be used safely in the food and fermentation industries, e.g., beer, wine, and bread making; those that can be used to control other microorganisms that might contaminate such production processes; those that can be used in biocontrol for food preservation; those than can be used for treatment of fungal infections in both humans and plants; and those that can be used in recombinant DNA technology. Such yeasts can include, but are not limited to, *Wickerhamomyces, Pichia* (e.g., *Pichia anomala, Pichia guielliermondii, Pichia kudrizvzevii) Hansenula, Saccharomyces, Hanseniaspora*, such as *Hanseniaspora uvarum, Ustilago maydis, Debaryomyces hansenii, Candida, Cryptococcus, Kluyveromyces, Torulopsis, Ustilago, Williopsis, Zygosaccharomyces*, such as *Zygosaccharomyces baili*, and others.

In other embodiments, the "microorganism" may be a cell culture such as, for example, an insect, nematode, or mammalian cell culture.

Target Plants Plants that can benefit from application of the products and methods of the subject invention include: Row Crops (e.g., Corn, Soy, Sorghum, Peanuts, Potatoes, etc.), Field Crops (e.g., Alfalfa, Wheat, Grains, etc.), Tree Crops (e.g., Walnuts, Almonds, Pecans, Hazelnuts, Pistachios, etc.), Citrus Crops (e.g., orange, lemon, grapefruit, etc.), Fruit Crops (e.g., apples, pears, etc.), Turf Crops, Ornamentals Crops (e.g., Flowers, vines, etc.), Vegetables (e.g., tomatoes, carrots, etc.), Vine Crops (e.g., Grapes, Strawberries, Blueberries, Blackberries, etc.), Forestry (eg, pine, spruce, eucalyptus, poplar, etc), Managed Pastures (any mix of plants used to support grazing animals).

The benefit can be in the form of, for example, increased yield, quality, disease and pest resistance, stress reduction (eg, from salt, drought, heat, etc) and improved water usage.

Further plants that can benefit from the products and methods of the invention include all plants that belong to the superfamily Viridiplantae, in particular monocotyledonous and dicotyledonous plants including fodder or forage legumes, ornamental plants, food crops, trees or shrubs selected from Acer spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida), Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsi-* cum spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

Further examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

Target Pests

The products and methods of the subject invention can be used to reduce damage caused by a wide range of pests.

Examples of such pests include Arthropods, including, for example, Lepidoptera (for example, Plutellidae, Noctuidae, Pyralidae, Tortricidae, Lyonetiidae, Carposinidae, Gelechiidae, Crambidae, Arctiidae, and Lymantriidae), Hemiptera (for example, Cicadellidae, Delphacidae, Psyllidae, Aphididae, Aleyrodidae, Orthezidae, Miridae, Tingidae, Pentatomidae, and Lygaiedae), Coleoptera (for example, Scarabaeidae, Elateridae, Coccinellidae, Cerambycidae, Chrysomelidae, and Curculionidae), Diptera (for example, Muscidae, Calliphoridae, Sarcophagidae, Anthomyiidae, Tephritidae, Opomyzoidea, and Carnoidea), Orthoptera (for example, Acrididae, Catantopidae, and Pyrgomorphidae), Thysanoptera (for example, Thripidae, Aeolothripidae, and Merothripidae), Tylenchida (for example, Aphelenchoididae and Neotylechidae), Collembola (for example, Onychiurus and Isotomidae), Acarina (for example, Tetranychidae, Dermanyssidae, Acaridae, and Sarcoptidae), Stylommatophora (for example, Philomycidae and Bradybaenidae), Ascaridida (for example, Ascaridida and Anisakidae), Opisthorchiida, Strigeidida, Blattodea (for example, Blaberidae, Cryptocercidae, and Panesthiidae) and Thysanura (for example, Lepismatidae, Lepidotrichidae, and Nicoletiidae).

Examples of the pests belonging to Lepidoptera include *Chilo suppressalis* Walker, *Cnaphalocrocis medinalis*, *Parnara guttata*, *Sesamia inferens*, *Mythimna separata*, *Naranga aenescens* Moore, *Spodoptera litura*, *Etiella zinckenella*, *Etiella behrii*, *Matsumuraeses falcana*, *Leguminivora glycinivorella*, *Pleuroptya naafis*, *Agrotis segetum*, *Agrotis ipsilon*, *Helcystogramma triannulellum*, *Xestia c-nigrum*, *Helicoverpa assulta*, *Helicoverpa armigera*, *Mamestra brassicae*, *Spodoptera exigua*, *Plutella xylostella*, *Pieris rapae*, *Pieris brassicae*, *Hellulla undalis*, and *Autographa nigrisigna*.

Examples of the pests belonging to Hemiptera include *Nilaparvata lugens*, *Sogatella furcifera*, *Laodelphax stratella*, *Nephotettix cincticeps*, *Recilia dorsalis*, *Stenotus rubrovittatus*, *Trigonotylus caelestialium*, *Leptocorisa chinensis*, *Nezara antennata*, *Nezara viridula*, *Lagynotomus elongatus*, *Scotinophara lurida*, *Eysarcoris annamita*, *Eysarcoris lewisi*, *Eysarcoris ventralis*, *Togo hemipterus* Scott, *Cletus punctiger*, *Piezodorus hybneri*, *Halyomorpha halys*, *Dolycoris baccarum*, *Neotoxoptera formosana*, *Rhopalosiphum padi*, *Rhopalosiphum maidis*, and *Aphis glycines*.

Examples of the pests belonging to Coleoptera include rice *Lissorhoptrus oryzophilus*, *Oulema oryzae*, *Echinocnemus squameus*, *Melanotus legatus*, *Melanotus fortnumi*, *Anomala cuprea*, *Popillia japonica*, *Maladera castanea*, *Epilachna varivestis*, *Paraluperodes nigrobilineatus*, *Epilachna vigintioctomaculata*, *Henosepilachna vigintioctopunctata*, *Harmonia axyridis*, *Anomala rufocuprea*, *Anomala testaceipes*, *Aulacophora indica*, and *Phyllotreta striolata*.

Examples of the pests belonging to Diptera include *Chlorops oryzae*, *Hydrellia griseola*, *Sitodiplosis mosellana*, *Delia platura*, *Asphondylia yushimai*, *Melanagromyza sojae*, *Liriomyza trifolii*, *Liriomyza sativae*, *Liriomyza huidobrensis*, and *Liriomyza bryoniae*.

Examples of the pests belonging to Orthoptera include *Oxya yezoensis* and *Oxya japonica*. Examples of the pests belonging to Thysanoptera include *Stenchaetothrips biformis* and *Thrips palmi*. Examples of the pests belonging to Tylenchida include *Meloidogyne*, Nematoda, and *Heterodera*. Examples of the pests belonging to Collembola include Onchiurus psuedamatus yagii and Onychiurus matsumotoi. Examples of the pests belonging to Acarina include *Penthaleus major*, *Tetranychus urticae*, *Tetranychus kanzawai*, *Tyrophagus putrescentiae*, and Tarsonemus bilobatus. Examples of the pests belonging to Stylommatophora include Helix and Philomycidae. Examples of the pests belonging to Ascaridida include *Ascaris lumbricoide*. Examples of the pests belonging to Opisthorchiida include *Metagonimus yokogawai*. Examples of the pests belonging to Strigeidida include *Schistosoma japonicum*. Examples of the pests belonging to Blattodea include *Blattella germanica*, *Periplaneta fuliginosa*, *Periplaneta americana*, and *Blatta lateralis*. Examples of the pests belonging to Thysanura include Ctenolepisma and *Lepisma*.

In one embodiment, the subject invention provides methods and products, based for controlling nematodes. Nematodes are a class of worms of the phylum Nemathelminthes roundworms or threadworms. Nematodes are also known as eelworms. Examples in the class are the cystforming nematodes of the genus *Heterodera*, the stubby root nematodes of the genus *Trichodorus*, the bulb and stem nematodes of the genus *Ditylenchus*, the golden nematode, *Heterodera rostochiensis*, the root knot nematodes, of the genus *Meloidogyne*, the root lesion nematodes of the genus *Pratylenchus*, the citrus nematodes of the genus *Tylenchulus*, the sting nematodes of the genus *Belonalaimus*, and the plant-parasitic nematodes of genera such as *Naccobus*, and *Radopholus*. In an exemplary embodiment, the method and products prevent formation of root galls caused by nematodes such as root knot and cyst nematodes.

Target Plant Disease

Examples of plant diseases, that can be controlled by the present invention, include the following:

Diseases of wheat: *Fusarium* head blight (*Fusarium graminearum*, *F. avenacerum*, *F. culmorum*, *Microdochium nivale*), Typhula snow blight (Typhula sp., *Micronectriella nivalis*), loose smut (*Ustilago tritici*, *U. nuda*), bunt (Tilletia caries), leaf blotch (*Mycosphaerella graminicola*), and glume blotch (*Leptosphaeria nodorum*);

Diseases of corn: smut (*Ustilago maydis*) and brown spot (*Cochliobolus heterostrophus*); Diseases of citrus: melanose (*Diaporthe citri*), scab (*Elsinoe fawcetti*), and *penicillium* rot (*Penicillium digitatum*, *P. italicum*);

Diseases of apple: blossom blight (*Monilinia mali*), powdery mildew (*Podosphaera leucotricha*), Alternaria leaf spot (*Alternaria alternata* apple pathotype), scab (*Venturia inaequalis*), bitter rot (*Colletotrichum acutatum*), and crown rot (*Phytophtora cactorum*);

Diseases of pear: scab (*Venturia nashicola*, *V. pirina*), black spot (*Alternaria alternata* Japanese pear pathotype), rust (*Gymnosporangium haraeanum*), and phytophthora fruit rot (*Phytophtora cactorum*);

Diseases of peach: brown rot (*Monilinia fructicola*), scab (*Cladosporium carpophilum*), and phomopsis rot (*Phomopsis* sp.);

Diseases of grape: anthracnose (*Elsinoe ampelina*), ripe rot (*Glomerella cingulata*), black rot (*Guignardia bidwellii*), downy mildew (*Plasmopara viticola*), and gray mold (*Botrytis cinerea*);

Diseases of Japanese persimmon: anthracnose (*Gloeosporium kaki*) and leaf spot (*Cercospora kaki*, *Mycosphaerella nawae*);

Diseases of gourd: anthracnose (*Colletotrichum lagenarium*), Target leaf spot (*Corynespora cassiicola*), gummy stem blight (*Mycosphaerella melonis*), Fusarium wilt (*Fusarium oxysporum*), downy mildew (*Pseudoperonospora cubensis*), and Phytophthora rot (*Phytophthora* sp.);

Diseases of tomato: early blight (*Alternaria solani*), leaf mold (*Cladosporium fulvum*), and late blight (*Phytophthora infestans*);

Diseases of cruciferous vegetables: Alternaria leaf spot (*Alternaria japonica*), white spot (*Cercosporella brassicae*), and downy mildew (*Peronospora parasitica*);

Diseases of rapeseed: sclerotinia rot (*Sclerotinia sclerotiorum*) and gray leaf spot (*Alternaria brassicae*);

Diseases of soybean: purple seed stain (*Cercospora kikuchii*), sphaceloma scad (*Elsinoe glycines*), pod and stem blight (*Diaporthe phaseolorum* var. *sojae*), rust (*Phakopsora pachyrhizi*), and brown stem rot (*Phytophthora sojae*);

Diseases of azuki bean: gray mold (*Botrytis cinerea*) and *Sclerotinia* rot (*Sclerotinia sclerotiorum*);

Diseases of kidney bean: gray mold (*Botrytis cinerea*), sclerotinia seed rot (*Sclerotinia sclerotiorum*), and kidney bean anthracnose (*Colletotrichum lindemthianum*);

Diseases of peanut: leaf spot (*Cercospora personata*), brown leaf spot (*Cercospora arachidicola*), and southern blight (*Sclerotium rolfsii*);

Diseases of potato: early blight (*Alternaria solani*) and late blight (*Phytophthora infestans*);

Diseases of cotton: *Fusarium* wilt (*Fusarium oxysporum*); Diseases of tobacco: brown spot (*Alternaria longipes*), anthracnose (*Colletotrichum tabacum*), downy mildew (*Peronospora tabacina*), and black shank (*Phytophthora nicotianae*);

Diseases of sugar beat: *Cercospora* leaf spot (*Cercospora beticola*), leaf blight (*Thanatephorus cucumeris*), Root rot (*Thanatephorus cucumeris*), and Aphanomyces root rot (*Aphanidermatum cochlioides*);

Diseases of rose: black spot (*Diplocarpon rosae*) and powdery mildew (*Sphaerotheca pannosa*);

Diseases of chrysanthemum and asteraceous plants: downy mildew (*Bremia lactucae*) and leaf blight (*Septoria chrysanthemi-indici*);

Diseases of various plants: diseases caused by *Pythium* spp. (*Pythium aphanidermatum*, *Pythium debarianum*, *Pythium graminicola*, *Pythium irregulare*, *Pythium ultimum*), gray mold (*Botrytis cinerea*), Sclerotinia rot (*Sclerotinia sclerotiorum*), and Damping-off (*Rhizoctonia solani*) caused by *Rhizoctonia* spp.;

Disease of Japanese radish: *Alternaria* leaf spot (*Alternaria brassicicola*);

Diseases of turfgrass: dollar spot (*Sclerotinia homeocarpa*), brown patch, and large patch (*Rhizoctonia solani*);

Disease of banana: sigatoka (*Mycosphaerella fijiensis*, *Mycosphaerella musicola*, *Pseudocercospora musae*); and Seed diseases or diseases in the early stages of the growth of various plants caused by bacteria of *Aspergillus* genus, *Penicillium* genus, *Fusarium* genus, *Tricoderma* genus, *Thielaviopsis* genus, *Rhizopus* genus, *Mucor* genus, *Phoma* genus, and *Diplodia* genus.

The disease may be root borne, foliar, present in the vascular system of the plant or transmitted by insects and include all bacterial, viral, and fungal pathogens of plants.

The plant disease control composition of the present invention can be applied to crop lands such as cultivated lands, paddy fields, lawns, and orchards, or non-crop lands. The plant disease control composition of the present invention can control plant diseases in and crop lands, in forests, in which "plants" are grown.

Target Weeds

As the weeds that can be controlled by the methods and compositions of the present invention, the following examples are given.

Weeds of the family Urticaceae: *Urtica urens*; weeds of the family Polygonaceae: *Polygonum convolvulus*, *Polygonum lapathifolium*, *Polygonum pensylvanicum*, *Polygonum persicaria*, *Polygonum longisetum*, *Polygonum aviculare*, *Polygonum arenastrum*, *Polygonum cuspidatum*, *Rumex japonicas*, *Rumex crispus*, *Rumex obtusifolius*, and *Rumex acetosa*; weeds of the family Portulacaceae: *Portulaca oleracea*; weeds of the family Caryophyllaceae: *Stellaria media*, *Cerastium holosteoides*, *Cerastium glomeratum*, *Spergula arvensis*, and *Silene gallica*; weeds of the family Molluginaceae: *Mollugo verticillata*; weeds of the family Chenopodiaceae: *Chenopodium album*, *Chenopodium ambrosioides*, *Kochia scoparia*, *Salsola kali*, and *Atriplex* spp.; weeds of the family Amaranthaceae: *Amaranthus retroflexus*, *Amaranthus viridis*, *Amaranthus lividus*, *Amaranthus spinosus*, *Amaranthus hybridus*, *Amaranthus palmeri*, *Amaranthus rudis*, *Amaranthus patulus*, *Amaranthus tuberculatos*, *Amaranthus blitoides*, *Amaranthus deflexus*, *Amaranthus quitensis*, *Alternanthera philoxeroides*, *Alternanthera sessilis*, and *Alternanthera tenella*; weeds of the family Papaveraceae: *Papaver rhoeas* and *Argemone mexicana*; weeds of the family Brassicaceae: *Raphanus raphanistrum*, *Raphanus sativus*, *Sinapis arvensis*, *Capsella bursa-pastoris*, *Brassica juncea*, *Brassica campestris*, *Descurainia pinnata*, *Rorippa islandica*, *Rorippa sylvestris*, *Thlaspi arvense*, *Myagrum rugosum*, *Lepidium virginicum*, and *Coronopus didymus*; weeds of the family Capparaceae: *Cleome affinis*; weeds of the family Fabaceae: *Aeschynomene indica*, *Aeschynomene rudis*, *Sesbania exaltata*, *Cassia obtusifolia*, *Cassia occidentalis*, *Desmodium tortuosum*, *Desmodiumadscendens*, *Trifolium repens*, *Pueraria lobata*, *Vicia angustifolia*, *Indigofera hirsute*, *Indigofera truxillensis*, and *Vigna sinensis*; weeds of the family Oxalidaceae: *Oxalis corniculata*, *Oxalis strica*, and *Oxalis oxyptera;* weeds of the family Geraniaceae: *Geranium carolinense* and *Erodium cicutarium*; weeds of the family Euphorbiaceae: *Euphorbia helioscopia*, *Euphorbia maculate*, *Euphorbia humistrata*, *Euphorbia esula*, *Euphorbia heterophylla*, *Euphorbia brasiliensis*, *Acalypha australis*, *Croton glandulosus*, *Croton lobatus*, *Phyllanthus corcovadensis*, and *Ricinus communis*; weeds of the family Malvaceae: *Abutilon theophrasti*, *Sida rhombiforia*, *Sidacordifolia*, *Sidaspinosa*, *Sidaglaziovii*, *Sida santaremnensis*, *Hibiscus trionum*, *Anoda cristata*, and *Malvastrum coromandelianum*; weeds of the family Sterculiaceae: *Waltheria indica*; weeds of the family Violaceae: *Viola arvensis*, and *Viola tricolor*; weeds of the family Cucurbitaceae: *Sicyos angulatus*, *Echinocystis lobata*, and *Momordica charantia*; weeds of the family Lythraceae: *Lythrum salicaria*; weeds of the family Apiaceae: *Hydrocotyle sibthorpioides*; weeds of the family Sapindaceae: *Cardiospermum halicacabum*; weeds of the family Primulaceae: *Anagallis arvensis*; weeds of the family Asclepiadaceae: *Asclepias syriaca* and *Ampelamus albidus*; weeds of the family Rubiaceae: *Galium aparine*, *Galium spurium* var. *echinospermon*, *Spermacoce latifolia*, *Richardia brasiliensis*, and *Borreria alata*; weeds of the family Convolvulaceae: *Ipomoea nil*, *Ipomoea hederacea*, *Ipomoea purpurea*, *Ipomoea hederacea* var. *integriuscula*, *Ipomoea lacunose*, *Ipomoea triloba*, *Ipomoea acuminate*, *Ipomoea hederifolia*, *Ipomoea coccinea*, *Ipomoea quamoclit*, *Ipomoea grandifolia*, *Ipomoea aristolochiafolia*, *Ipomoea cairica*, *Convolvulus arvensis*, *Calystegia hederacea*, *Calystegia japonica*, *Merremia hedeacea*, *Merremia aegyptia*, *Merremia cissoids*, and *Jacquemontia tamnifolia*; weeds of the family Boraginaceae: *Myosotis arvensis*; weeds of the family Lamiaceae: *Lamium purpureum*, *Lamium amplexicaule*, *Leonotis nepetaefolia*, *Hyptis suaveolens*, *Hyptis lophanta*, *Leonurus sibiricus*, and *Stachys arvensis*; weeds of the family Solanaceae: *Datura stramonium*, *Solanum nigrum*, *Solanum americanum*, *Solanum ptycanthum*, *Solanum sarrachoides*, *Solanum rostratum*, *Solanum aculeatissimum*, *Solanum sisymbriifolium*, *Solanum carolinense*, *Physalis angulata*, *Physalis subglabrata*, and *Nicandra physaloides*; weeds of the family Scrophulariaceae: *Veronica hederaefolia*, *Veronica persica*, and *Veronica arvensis*; weeds of the family Plantaginaceae: *Plantago*

*asiatica*; weeds of the family Asteraceae: *Xanthium pensylvanicum, Xanthium occidentale, Helianthus annuus, Matricaria chamomilla, Matricaria perforate, Chrysanthemum segetum, Matricaria matricarioides, Artemisia princeps, Artemisia vulgaris, Artemisia verlotorum, Solidago altissima, Taraxacum officinale, Galinsoga ciliate, Galinsoga parviflora, Senecio vulgaris, Senecio brasiliensis, Senecio grisebachii, Conyza bonariensis, Conyza Canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis*, and *Soliva sessilis*; weeds of the family Liliaceae: *Allium canadense* and *Allium vineale*; weeds of the family Commelinaceae: *Commelina communis, Commelina bengharensis*, and *Commelina erecta*; weeds of the family Poaceae: *Echinochloa crusgalli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum*, and *Rottboellia cochinchinensis*; weeds of the family Cyperaceae: *Cyperus microiria, Cyperus iria, Cyperus odoratus, Cyperus rotundus, Cyperus esculentus*, and *Kyllinga gracillima*; and weeds of the family Equisetaceae: *Equisetum arvense* and *Equisetum palustre*; and the like.

EXAMPLES

It should be understood that the examples and embodiments described herein are for illustrative purposes only and that various modifications or changes in light thereof will be suggested to persons skilled in the art and are to be included within the spirit and purview of this application.

Example 1: Fermentation of *Starmerella bombicola* for Sophorolipid (SLP) Production in a 110 L Distributable Reactor A portable, airlift-type, fully enclosed reactor operated by PLC with water filtration, temperature control unit, and an air blower on board is used. The reactor has a working volume of 90 L when growing *S. bombicola* for SLP production.

In preferred embodiments, the nutrients for SLP production are glucose, urea, yeast extract, canola oil, magnesium sulfate, and potassium phosphate.

The reactor is inoculated with 8 liters of liquid culture grown in flasks. The duration of the cultivation cycle for SLP production is 7-8 days, at 25° C. and pH 3.5, with sampling performed twice a day.

The final concentration of SLP is roughly 10% of working volume, in this case about 9 L of product, containing 300-400 grams of SLP per liter.

Example 2: Fermentation of *Wickerhamomyces* and/or *Pichia* Yeast for Sophorolipid Production in a 450 L Distributable Reactor A movable airlift reactor operated by PLC with water filtration, temperature control unit, and air blower for sufficient aeration is used. The process can be carried out as batch cultivation process. The reactor has a working volume of 400 L when growing *Wickerhamomyces* or *Pichia* for SLP production.

In preferred embodiments, the nutrients for SLP production are glucose, urea, yeast extract, canola oil, magnesium sulfate, and potassium phosphate.

Inoculation of this reactor requires up to 5% liquid seed culture of working volume. The duration of the cultivation cycle is 7 days, at a temperature 25° C. and pH 3.5, with sampling performed twice a day.

The final concentration of SLP is roughly 20-25% of the working volume, in this case greater than 90 L of product forms.

Example 3: Fermentation of *Wickerhamomyces* and/or *Pichia* Yeast for Cell and Single Cell Protein Production in 900 L Distributable Reactor A portable reactor divided into two tanks run by a central airlift to help mix the two tanks simultaneously is used. The reactor has a working volume of 600 L when growing *Wickerhamomyces* and/or *Pichia* for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach 90 kilos per cycle with protein concentration up to 45 kilos.

Example 4: Fermentation of *Wickerhamomyces* and/or *Pichia* Yeast for Cell and Single Cell Protein Production in 2000 L Distributable Reactor A portable reactor divided into two square tanks accompanied with 2 loops for mass exchange between them is used. The reactor has a working volume of 2000 L when growing *Wickerhamomyces* and/or *Pichia* for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach up to 200 kilos per cycle with protein concentration up to 100 kilos.

Example 5: Synergistic Fermentation of a Combined Culture of *Acinetobacter venetianus* and *Bacillus subtilis* in a 900 L Distributable Reactor A portable reactor divided into two tanks run by a central airlift to help mix the two tanks simultaneously is used. The reactor has a working volume of 600 L when growing *Acinetobacter/Bacillus subtilis* for biosurfactant production.

In a preferred embodiment, the nutrients for biosurfactant production are glucose, powder molasses, sucrose, potassium phosphate, sodium phosphate, potassium chloride, magnesium sulfate, calcium chloride, urea, ammonium chloride, and yeast extract.

The reactor containing 600 L of nutrient medium with pH 6.8-7.0 is inoculated with 60 liters of seed culture containing both *Acinetobacter* and *Bacillus subtilis*. Fermentation continues for 24 hours with no pH stabilization, and a temperature of 28 to 30° C.

The final concentration of cells will be up to 1 billion cells of combined culture with approximate equal distribution of both microorganisms.

Example 6: Fermentation of *Starmerella bombicola* for Sophorolipid Production in Portable 14 L Distributable Reactor This reactor is an autoclavable jacketed glass vessel with air spurge and impeller. It is equipped with dissolved oxygen, pH, temperature, and foam prob; it has an integrated control station with a color touchscreen interface, built-in pumps, gas flow controllers, and pH/DO foam/level controllers.

The working volume of the reactor is 10 liters.

Nutrient medium contains glucose, yeast extract, urea, and vegetable oil. Inoculum can be a 1 to 2-day old culture of *Starmerella bombicola* at about 5-10% of the total culture volume. Cultivation duration and readymade product collection continues for 5-14 days. Final sophorolipid production can reach 1-2 kilogram per cycle.

Example 7: Fermentation of *Pseudozyma aphidis* for Mannosylerythritol Lipid (MEL) Production in Portable 14 L Distributable Reactor This is a steam autoclavable jacketed glass vessel with air spurge and Rushton impeller. It is equipped with DO, pH, temperature, and foam probe. It has an integrated control station with a color touchscreen interface, built-in pumps, gas flow controllers, and pH/DO foam/level controllers. The working volume of the reactor is 10 liters.

Nutrient medium composition: Sodium nitrate, Potassium phosphate, Magnesium sulfate, yeast extract, and vegetable oil. Inoculum can be a 1 to 2 day old culture of *Pseudozyma aphidis*, at about 5-10% of the total culture volume. Cultivation duration and sample collection: 9-15 days. Final MEL production: 800-1000 grams.

Example 8: Cultivation of *Bacillus subtilis* in Distributable Hybrid System This is a hybrid system between liquid state fermentation and solid state fermentation. In this system a large number of individual nutrient medium-saturated hydrophilic particles are suspended in a matrix of hydrophobic particles. The hydrophilic particles can be, for example, fumed silica, perlite, vermiculite, or diatomaceous earth. Hydrophobic particles can be, for example, polymer coated sand (hydrophobic sand), perlite, vermiculite.

Embedment of hydrophilic particles in hyphobic particles creates a sterile microculture environment. Also, the hydrophobic matrix allows efficient gas exchange for the cultures. Working volume: 500 ml-1 metric ton.

Nutrient medium composition: Nutrient broth, M9 media, Tryptic soy broth. Types of inoculum and its amount: Inoculum can be 12 hr-16 hr old about 1-5% of the total culture volume. Cultivation duration: 1-3 days. Final CFU: 1-2 billion cells/spore per 1 gram.

Example 9: Cultivation of *Trichoderma harzianum* in Distributable Hybrid System A similar method was developed for the cultivation of *Mycorrhiza* utilizing hydrophobic sand and diatomaceous earth as described in Example 8. This system has, by weight, 1 part of diatomaceous earth saturated with nutrient medium, homogenized in 6 parts of hydrophobic sand. A powdered inoculum was then added. This mixture was allowed to incubate under optimal fungal growth conditions. The sample was enumerated daily.

Working volume: 100 ml to 1 metric ton. Nutrient medium composition: Potato dextrose broth and soy peptone. Types of inoculum and its amount: Dry spore or mycelial propagules. Cultivation duration: 7-10 days. Final mass production: up to $10^9$ propagules/gram.

Example 10: Preparation of Sophorolipid Soil Amendment

For this invention, a natural mixture of sophorolipids was synthesized by fermentation of *S. bombicola* in a fermentation medium containing 100 g/L glucose, 10 g/L yeast extract, 1 g/L urea and 100 ml/L canola oil in water. After 5-7 days of fermentation, approximately 500 g/L of sophorolipid precipitated as a brown colored layer at the bottom of the fermentation vessel.

The sophorolipid layer was collected and diluted 4-fold to a SLP concentration of 125 g/L. The pH was adjusted to 6.5-7.0 using sodium hydroxide. Advantageously, the sophorolipid broth also contains some residual yeast cells and trace amounts of metabolites and media components. This allows for the presence of high concentrations of mannoprotein as a part of yeast cell wall's outer surface (mannoprotein is a highly effective bioemulsifier capable of reaching up to an 80% emulsification index); the presence of biopolymer beta-glucan (an emulsifier) in yeast cell walls; the presence of sophorolipid in the culture; and the presence of solvents and/or other metabolites (e.g., lactic acid, ethanol, etc.).

Two different products can be produced from this fermentation process: one comprising the pure SLP layer and one comprising the entire broth containing *S. bombicola* culture and SLPs.

All patents, patent applications, provisional applications, and publications referred to or cited herein are incorporated by reference in their entirety, including all figures and tables, to the extent they are not inconsistent with the explicit teachings of this specification.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Use of the term "comprising," herein includes consisting essentially of" and "consisting of" The term "consisting essentially of," as used herein, limits the scope of the ingredients and steps to the specified materials or steps and those that do not materially affect the basic and novel characteristic(s) of the present invention, e.g., compositions and methods for promoting plant health. The term "consisting essentially of," as used herein, limits the scope of the ingredients and steps to the specified materials or steps and those that do not materially affect the basic and novel characteristic(s) of the present invention.

We claim:

1. A method for providing a microbe-based product selected from the group consisting of microbes, a broth in which the microbes were grown, a biosurfactant produced by the microbes, and combinations thereof, wherein said method comprises growing the microbes in a microbe growth facility, harvesting said microbes, broth and/or biosurfactant, creating said microbe-based product from said harvested microbes, broth and/or biosurfactant, and transporting the microbe-based product to a location for use;

wherein the biosurfactant is selected from the group consisting rhamnolipids, sophorolipids (SLP) and mannosylerythritol lipids (MEL);

wherein said microbes are selected from the group consisting of *Pseudomonas aeruginosa, Starmerella bombicola, Pichia anomala, Wickerhamomyces anomalus, Trichoderma harzianum, Bacillus amyloliquefaciens, Bacillus subtilis*, and *Pseudozyma aphidis;* wherein said microbe growth facility comprises a plurality of independent modular growth vessels in which the same, or different, microbes grow, under the same, or different, growth conditions that can be varied between the independent growth vessels;

wherein at least one of the growth conditions that can be varied between the independent modular growth vessels is selected from the group consisting of growth medium, oxygenation, pH, agitation, and temperature; and wherein said transport of the microbe-based product is in a container having a volume of 1 gallon to 1,000 gallons, or via a conduit.

2. The method, according to claim 1, wherein a cellular mass of the microbes in the transported microbe-based product is less than 50% of the total weight of the microbe-based product.

3. The method, according to claim 1, wherein the microbes that are grown at the microbe growth facility are sourced from a location at which the microbe-based product will be used.

4. The method, according to claim 1, wherein the microbe-based product is the microbes and broth in which the microbes were grown.

5. The method, according to claim 1, further comprising applying the microbe-based product to a site and/or an environment selected from the group consisting of: soil, agricultural pests, weeds, seeds, plants, plant roots, animals, animal waste, animal feed, ore, an oil spill, a hazardous waste site, an oil well, an oil rig, an oil piping, and oil tanks.

6. The method, according to claim 5, wherein the site is selected from the group consisting of soil, agricultural pests, weeds, seed, plants, or plant roots; and wherein said applying is done via an irrigation system.

7. The method, according to claim 5, wherein the method further comprises monitoring, after said applying, at least one of: the abundance of the microbe-based product at the site to which it has been applied, or movement of the microbe-based product through the site to which it has been applied.

8. The method, according to claim 5, wherein the site is selected from the group consisting of seeds, plant leaves, and plant roots, and where the method further comprises monitoring a measure of plant health and/or yield.

9. The method, according to claim 1, wherein, the microbe-based product is transported in a spore state.

10. The method, according to claim 1, wherein the microbe-based product is a biosurfactant.

11. The method, according to claim 10, wherein the biosurfactant is produced by *Starmerella bombicola.*

12. The method, according to claim 1, wherein the microbe-based product is an animal feed.

13. The method, according to claim 5, which further comprises monitoring a measure of plant health and/or yield of a plant to which the microbe-based product has been applied.

14. The method of claim 5, applied to improve water drainage.

15. The method of claim 5, applied to improve aeration and/or porosity of compacted soil.

* * * * *